United States Patent [19]

Trick

[11] 4,419,985

[45] Dec. 13, 1983

[54] APPARATUS FOR REVERSIBLY CLOSING A BODY PASSAGE

[75] Inventor: Robert E. Trick, Racine, Wis.

[73] Assignee: Medical Engineering Corporation, Racine, Wis.

[21] Appl. No.: 361,466

[22] Filed: Mar. 24, 1982

Related U.S. Application Data

[63] Continuation of Ser. No. 182,468, Aug. 28, 1980, abandoned.

[51] Int. Cl.³ .................... A61F 1/00; A61B 17/00
[52] U.S. Cl. .............................. 128/1 R; 128/346; 128/DIG. 25; 3/1
[58] Field of Search .......... 128/346, 325, 344, 349 B, 128/DIG. 25, 327; 3/1, 1.2; 92/40, 34; 417/389, 472; 222/386.5

[56] References Cited

U.S. PATENT DOCUMENTS

| | | |
|---|---|---|
| 2,533,924 | 12/1950 | Foley . |
| 2,637,167 | 5/1953 | Barradell-Smith et al. ........ 92/40 X |
| 2,847,032 | 8/1958 | Fleming ................. 92/40 X |
| 3,215,084 | 11/1965 | Cline ................... 92/40 X |
| 3,538,917 | 11/1970 | Selker . |
| 3,575,158 | 4/1971 | Summers . |
| 3,730,186 | 5/1973 | Edmunds, Jr. et al. . |
| 3,731,670 | 5/1973 | Loe . |
| 3,750,194 | 8/1973 | Summers . |
| 3,815,576 | 6/1974 | Balaban . |
| 3,863,622 | 2/1975 | Buuck . |
| 4,222,377 | 9/1980 | Burton . |

FOREIGN PATENT DOCUMENTS

2383673 11/1978 France ........................... 128/325

Primary Examiner—Michael H. Thaler
Attorney, Agent, or Firm—Quarles & Brady

[57] ABSTRACT

An implantable apparatus for controlling the flow of body fluids through a body passage includes a cuff which can be inflated with pressurizing fluids to close the body passage, a push button actuated and expandible reservoir for the pressurizing fluid and tubing connecting the cuff and the reservoir to form a closed system. The reservoir includes a pumping chamber having a tension spring positioned therein and a push rod located outside the pumping chamber. The push rod is attached to a push button which when actuated expands the volume of the reservoir to receive pressurizing fluids from the cuff thereby allowing the cuff to deflate and the body passage to open.

2 Claims, 9 Drawing Figures

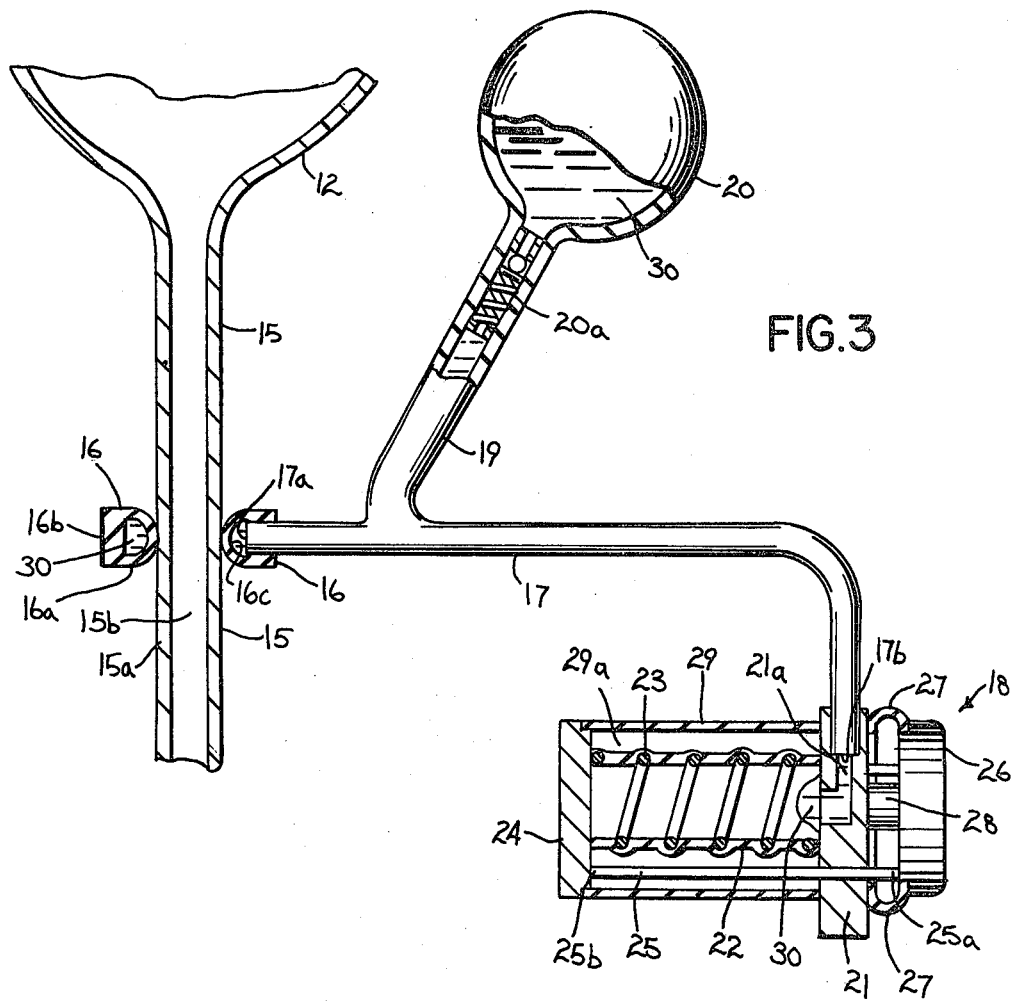
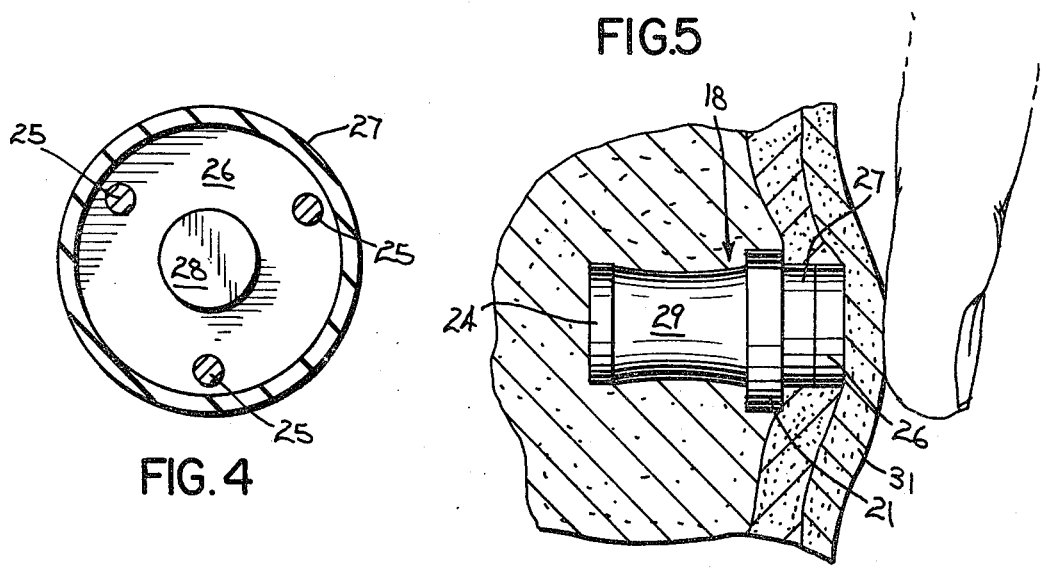

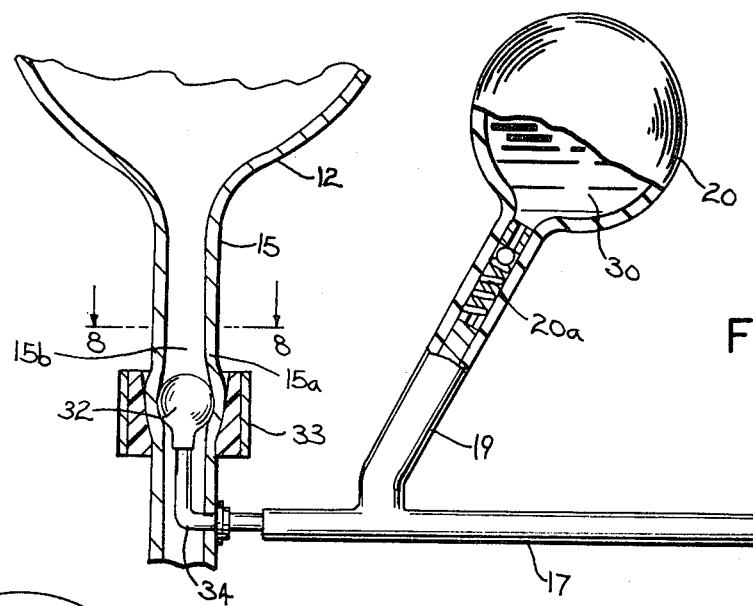
FIG.6
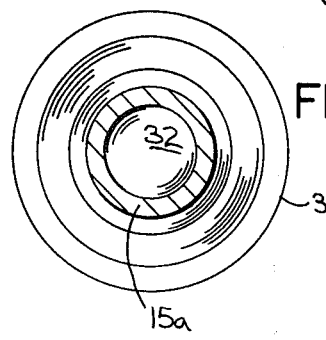
FIG.8
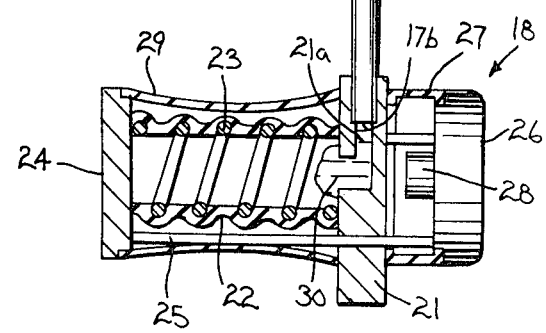
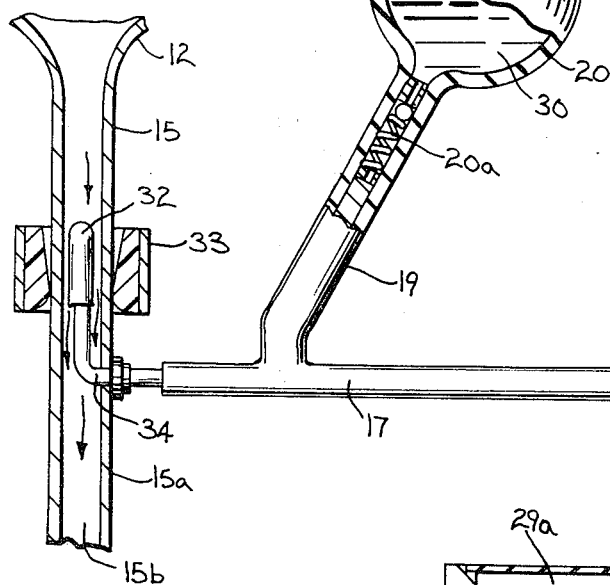
FIG.7
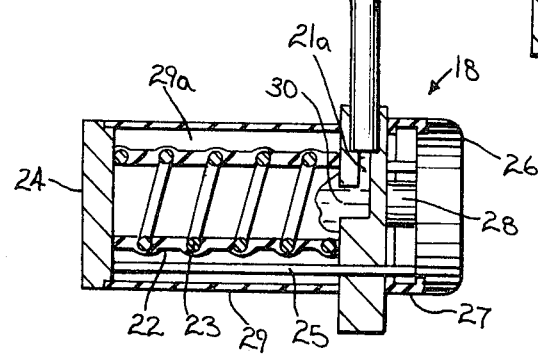
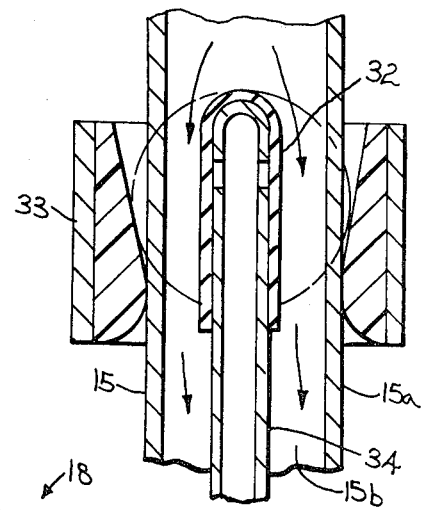
FIG.9

APPARATUS FOR REVERSIBLY CLOSING A BODY PASSAGE

This is a continuation, of application Ser. No. 182,468, filed Aug. 28, 1980 now abandoned.

The present invention relates to an apparatus and method for reversibly closing a body passage. More particularly, it relates to an implantable apparatus which serves as a sphincter for controlling the disharge of urine from the bladder.

BACKGROUND OF THE INVENTION

Many persons suffer from non-functioning or malfunctioning sphincters which are circular bands of voluntarily or involuntarily controlled muscles which encircle an orifice of the body or body canal or one of the body's hollow organs. This condition can be caused by congenital malformations, trauma to the sphincter nerves or muscles, or disease of the sphincter nerves or muscles.

One of the most troublesome and embarrassing conditions brought about by the lack of proper control of one or more sphincters is the malfunctioning of the urethral sphincter. The urethral sphincter controls the retention of urine in the bladder until the sphincter is relaxed to permit passage of urine from the bladder. As a result of the malfunctioning of the urethral sphincter, uncontrolled drainage of urine from the body can occur. This is embarrassing to the individual and can restrict his activities.

Attempts have been made in the past to provide a substitute for a malfunctioning urethral sphincter and to provide some means for controlling artificial openings that have no natural sphincters. Various types of inflatable devices have been proposed that are insertable into a natural or artificial body passage from outside the body and which can be inflated to obstruct the artificial or natural passage so that seepage does not occur from the passage. Various surgical procedures also have been attempted to repair damaged and diseased sphincters and electric currents have been used in attempts to cause the sphincters to either contract or relax at the proper time. In addition, various control devices have been implanted for use as artificial sphincters.

None of the prior art attempts have been completely successful. Therefore, a need still exists for an improved apparatus and method for reversibly closing body passages.

SUMMARY OF THE INVENTION

The present invention relates to an apparatus and a method for reversibly closing a body passage and more particularly to an apparatus and method for controlling the discharge of urine from the bladder.

It is an object of the present invention to provide an implantable apparatus that can efficiently and reversibly close a body passage.

It is also an object of the present invention to provide an implantable apparatus that is readily operable by the individual in whom it is implanted to reversibly close a body passage.

It is further an object of the present invention to provide an implantable apparatus that is cosmetically and psychologically acceptable to the person in whom it is implanted.

It is more specifically an object of the present invention to provide an implantable apparatus that can reversibly close a urinary passage.

It is also an object of the present invention to provide a method for reversibly closing a natural or implanted body passage that utilizes implantable inflatable means.

It is also an object of the present invention to provide a method for reversibly closing a urinary passage.

The present invention provides an implantable control apparatus for controlling the flow through a body passage that includes inflatable means which is normally inflated with hydraulic fluid under pressure to cut off flow through the body passage, an expandable reservoir of hydraulic fluid, tubing connecting the reservoir to the inflatable means to form a closed system, and means for expanding said reservoir to increase its effective volume so that the hydraulic fluid under pressure in the inflatable means will flow to the expanded reservoir and the inflatable means will be deflated to open the body passage to flow.

The present invention also provides a method for reversibly closing a body passage which includes the steps of implanting inflatable means where it can, when inflated, cut off flow through the body passage, also implanting an expandable reservoir of hydraulic fluid and connecting the reservoir to the inflatable means with tubing, if not done previously, to form a closed system, filling the system, if not done previously, with hydraulic fluid under pressure to inflate the inflatable means, and positioning means for expanding the reservoir at a convenient spot under the patient's skin so that it can be actuated by the patient from without his body to expand the reservoir, deflate the inflatable means and open the body passage.

The method further includes the steps of re-inflating the inflatable means to close the body passage when desired.

In one embodiment of the apparatus the inflatable means is a cuff which is positioned about the flexible wall of the body passage and which can be inflated to collapse the wall of the body passage to stop flow. In another embodiment, the inflatable means is a balloon positioned in the body passage. The balloon when inflated occludes the lumen of the body passage.

In another embodiment, the apparatus also includes a second reservoir of hydraulic fluid which communicates with and is part of the closed system. The second reservoir is equipped with a check valve which automatically opens to replenish the supply of fluid in the system if the pressure in the system drops below a useful level.

BRIEF DESCRIPTION OF THE DRAWINGS

The invention will be hereinafter more fully described with reference to the accompanying drawings in which:

FIG. 3 is a view similar to FIG. 2 with the body passage open;

FIG. 4 is a view taken along lines 4—4 in FIG. 2;

FIG. 5 is an enlarged sectional view illustrating how the apparatus can be actuated through the skin;

FIG. 6 is a view similar to FIG. 2 of a second embodiment of the apparatus of the present invention with the body passage closed;

FIG. 7 is a view similar to FIG. 6 with the body passage open;

FIG. 8 is a view taken along lines 8—8 in FIG. 6; and

FIG. 9 is an enlarged view of the inflatable means, body passage and collar of FIG. 7.

DESCRIPTION OF THE PREFERRED EMBODIMENTS

The first embodiment of the invention is shown in FIGS. 1 to 5.

Figure 1:
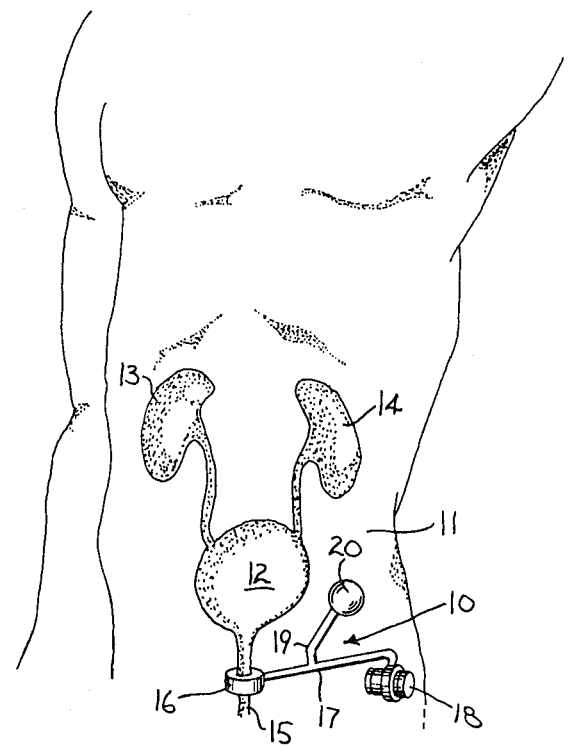
FIG. 1 is a diagrammatic view of one embodiment of the apparatus of the present invention implanted within the body of a human.

Referring to FIG. 1, there is seen a preferred embodiment of the apparatus of the present invention for opening and closing a body passage, generally designated as 10, implanted within a human body 11. A bladder 12 connected to a pair of kidneys 13, 14 can also be seen. The bladder 12 may be a natural urinary bladder or an implanted artificial urinary bladder. Connected to the bladder 12 is the urethra 15 through which urine flows to the outside. Normally, the urethra 15 is opened or closed by one or more sphincters (not shown) which are controlled by voluntary nerve impulses. It should be understood that any reference to the words "bladder" and "urethra" in this application is intended to include both the natural or artificial bladder and urethra or any other suitable natural or artificial structures which perform similar body functions.

Figure 2:
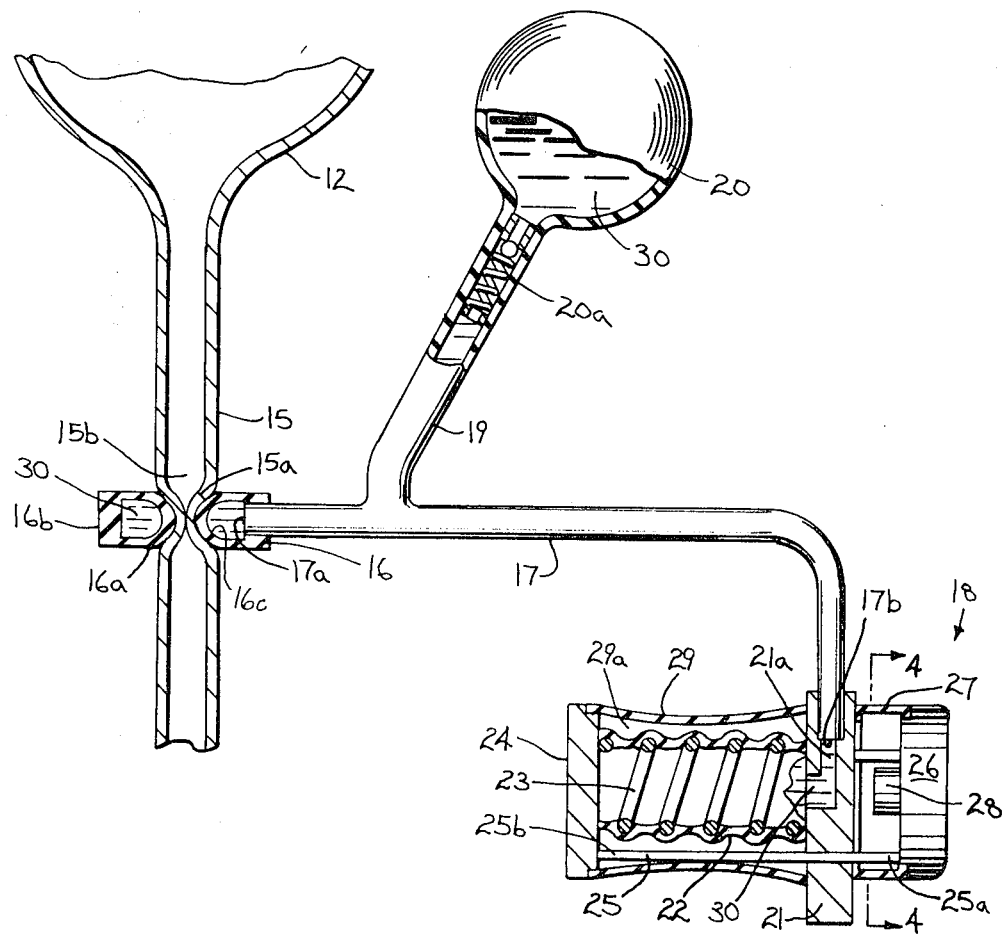
FIG. 2 illustrates, on a larger scale and partially in section, the apparatus in FIG. 1 with the body passage closed.

Referring to FIGS. 2 and 3, it can be seen that surrounding the urethra 15 is an inflatable cuff 16 which is connected by tubing 17 to a push-button actuated expandable fluid reservoir 18. Positioned intermediate the length of the tubing 17 between the cuff 16 and the reservoir 18 is a branch 19 of the tubing 17 which leads to a second fluid reservoir 20. The second reservoir 20 is provided with a check valve 20a. When pressure in the closed system falls below a desired level, the check valve 20a opens to permit additional fluid to enter the system and to restore the pressure to the desired level.

In FIG. 2, it can be seen that when the cuff 16 is inflated the cylindrical wall 15a of the urethra 15 is collapsed, closing the internal lumen 15b of the urethra 15 so that no fluid can flow therethrough. As seen in FIG. 3, when the cuff 16 is deflated the normal resiliency of the wall 15a of the urethra 15 keeps the urethra lumen 15b open.

The components of the apparatus 10 which controls the flow through the body passage will be described in connection with FIGS. 2 to 5.

In the embodiment shown in FIGS. 2 to 5, the actual closing and opening of the urethra 15 is accomplished by inflating the cuff 16 to collapse the wall 15a of the urethra 15 (as seen in FIG. 2). Although the cuff 16 has been referred to as inflatable, it does not have to be elastic as the term is normally understood. However, it is necessary that the cuff 16 have a readily deformable inner wall 16a.

As can be seen in FIGS. 2 and 3, the deformable wall 16a is thinner and thus more elastic and deformable than the outer wall 16b. However, it will be appreciated that the difference in deformability of the walls 16a and 16b can be achieved by other techniques than varying the thickness, e.g. making 16b of a less flexible or elastic material. Still referring to FIGS. 2 and 3 it can be seen that one end 17a of the tubing 17 extends into and is in fluid communication with an inner chamber 16c of the cuff 16. The other end 17b of the tubing 17 is connected to the expandable fluid reservoir 18.

As seen best in FIGS. 2, 3 and 4, the push-button actuated expandable fluid reservoir 18 includes a mount 21, a collapsible cylindrical pump chamber 22, a tension coil spring 23, an end cap 24, push rods 25, a push button 26, a flexible cover 27 for the push button, a stop 28 and a flexible collapsible protective cover 29 for the pump chamber 22. The protective cover 29, the push button 26, the mount 21 and the cover 27 cooperate to form a fluid reservoir 29a about the pump chamber 22. The fluid reservoir 29a collects and retains any fluid which leaks from the pump chamber 22 and might otherwise be lost. The spring 23 is positioned within the collapsible cylindrical pump chamber 22 between the end cap 24 and the mount 21.

The push rods 25 are attached at one end 25a to the underside of the push button 26 and at the other end 25b contact the end cap 24. As seen only in FIG. 4 there are three push rods 25. When the push button 26 is forcibly depressed and held in a depressed condition as seen in FIG. 3, the push rods 25 move the end cap 24 further away from the mount 21 stretching the spring 23 and thus expanding the internal volume of the pump chamber 22. The increase in volume of the pump chamber 22 has the effect of decreasing the fluid pressure in the pressurized closed system 10 which causes the cuff 16 to deflate sufficiently to allow the resilient wall 15a of the urethra 15 to move outwardly and the lumen 15b to open as seen in FIG. 3. As soon as the push button 26 is released, the spring 23 forcibly pulls the end cap 24 back towards the mount 21, collapsing and reducing the effective volume of the pumping chamber 22 and forcing fluid 30 through the passage 21a in the mount 21 which connects the interior of the pumping chamber 22 to the tubing 17. When the pumping chamber 22 is collapsed, the fluid 30 displaced from the chamber 22 inflates the cuff 16 and closes the urethra 15. The inward movement of the push button 26 is limited by the stop 28 to the extent required to expand the volume of the chamber 22 sufficiently to deflate the cuff 16. When the bladder 12 is emptied, the push button 26 is released and the cuff 16 reinflates to close the urethra 15.

As seen in FIGS. 1 and 5, the push button 26 is positioned just below the skin 31 of the patient so that it can be depressed from outside by exerting digital pressure on the push button 26 in the manner shown in FIG. 5.

The second embodiment of the apparatus of the present invention is seen in FIGS. 6 to 9. As seen therein, the second embodiment differs from the embodiment of FIGS. 1 to 4 primarily in that the inflatable means used to close the body passage, instead of being a cuff, is a balloon 32 adapted to be positioned within the lumen 15b of the urethra 15. The tubing 17, and the first reservoir 18 and second optional reservoir 20 are similar in function and structure to those of the first embodiment.

Although the balloon 32 can be used by itself to occlude the lumen 15b, it is preferably used in conjunction with a relatively rigid tapered collar or seat 33 as seen best in FIG. 6. The seat 33 which is positioned about the outside wall of the urethra 15 serves to prevent the flexible urethra wall 15a from being expanded or stretched and potentially damaged by the inflated balloon 32. The balloon 32 is connected by an angle tube 34 to tubing 17 which in turn is connected to the reservoir 18 in the manner previously described for the first embodiment.

When the push button 26 is actuated in a manner similar to that shown in FIG. 5, the collapsible pump chamber 22 is expanded by the push rods 25, the balloon 32 deflates and the lumen 15b of the urethra 15 is opened to fluid flow as seen in FIGS. 7 and 9. Upon release of the push button 26, the spring 23 forcibly contracts or collapses the pumping chamber 22 by pulling the end cap 24 towards the mount 21 thus forcing hydraulic fluid 30 through the passage 21a of the mount 21 and the tubing 17 to re-inflate the balloon 32 and close the urethra 15 as seen in FIGS. 6 and 8.

Prior to implanting either of the described embodiments, the closed systems are initially filled with hydraulic fluid under a slight pressure. The fluid preferred for this purpose is of physiological saline. The hydraulic fluid selected must be physiologically compatible with body tissue and body organs in the event that a leak would develop in the system.

The non-metallic components of the apparatus of the present invention are preferably made of medical grade polymer such as silicone rubber, and the fluid-tight connections between the various components are preferably made with an implantable grade of silicone adhesive of which several types are commercially available. The metallic components such as the spring are also preferably made of a biopcompatible material such as stainless steel.

The apparatus of the present invention preferably is implanted completely within the patient's body. This may be done by making a suitable incision through the skin so as to provide access to the abdominal cavity. With the abdominal cavity opened, the urethra can be exposed and the cuff or balloon properly positioned. The other components may be arranged generally as shown in FIG. 1 and the abdominal cavity surgically closed, The manner of the implantation described is generic for both males and females. The systems disclosed are sufficiently versatile to allow implanting in various regions of the body. For example, for some male patients it may be preferable to implant the push-button actuated expandable reservoir in the patient's scrotum.

It will be appreciated by those skilled in the art that the foregoing description of the preferred embodiments for use in controlling the urethra has been for purposes of illustration only. The apparatus and the method of the present invention can be used to control flow through other body passages such as the colon. Therefore, it is intended that the scope of the invention not be limited except by the claims which follow.

I claim:

1. In an apparatus for implantation in a patient's body to control the flow of a body fluid through a body passage, wherein the apparatus has an inflatable means which can be inflated to close the body passage and deflated to open the body passage, and tubing connected at one end to the inflatable means to carry hydraulic fluid to and from the inflatable means, the improvement which comprises a push button actuated and expandable hydraulic fluid reservoir assembly also adapted to be implanted within the body which assembly includes:
   (a) a support coupled to the other end of said tubing, said support having a passage therethrough for conveying hydraulic fluid;
   (b) a rigid cap spaced from the support;
   (c) an elongated pumping chamber extending from the support to the cap and attached to the cap, said chamber communicating with said passage in the support to receive and transmit hydraulic fluids and containing a substantial amount of hydraulic fluid even in its unexpanded state;
   (d) a tension spring positioned within said pumping chamber and extending longitudinally between the support and the cap, said tension spring preventing the pumping chamber from being completely collapsed and emptied of hydraulic fluid in its unexpanded state;
   (e) a push rod connected at one end to said cap and having the other end extending through and past the support, said push rod being located outside of the pumping chamber; and
   (f) a push button mounted at the other end of the push rod; and wherein said inflatable means, said tubing, said support passage and said pumping chamber form a closed system adapted to contain a pressurized fluid, so that when said push button is actuated said push rod will move said cap and thereby expand said pumping chamber from an initial volume containing a substantial amount of hydraulic fluid to a larger volume which will accommodate an added volume of hydraulic fluid from the inflatable means and cause said inflatable means to deflate due to the flow of hydraulic fluid through said tubing from said inflatable means to said pumping chamber.

2. The improvement of claim 1 further comprising a flexible cover means extending from the push button to the cap and completely around said pumping chamber and said push rod to define a secondary chamber for containing any leaks from the pumping chamber.

* * * * *